United States Patent [19]

Brummond et al.

[11] Patent Number: 5,578,457
[45] Date of Patent: *Nov. 26, 1996

[54] IMMUNOASSAYS WITH NOVEL LABELED CARBAMAZEPINE HAPTEN ANALOGUES

[75] Inventors: Barbara A. Brummond, Rochester; Mohan S. Saini; Ignazio S. Ponticello, both of Pittsford, all of N.Y.

[73] Assignee: Johnson & Johnson Clinical Diagnostics, Inc., Rochester, N.Y.

[*] Notice: The term of this patent shall not extend beyond the expiration date of Pat. No. 5,543,311.

[21] Appl. No.: 926,202

[22] Filed: Aug. 7, 1992

[51] Int. Cl.$^6$ .............................. G01N 33/545; C12N 9/96
[52] U.S. Cl. ........................ 435/7.93; 435/188; 436/815
[58] Field of Search ................................ 435/7.93, 188; 436/815

[56] References Cited

U.S. PATENT DOCUMENTS

| | | | |
|---|---|---|---|
| 4,058,511 | 11/1977 | Singh | 436/543 |
| 4,404,366 | 9/1983 | Boguslaski et al. | 536/5 |
| 4,442,204 | 4/1984 | Greenquist et al. | 435/7.7 |
| 4,476,229 | 10/1984 | Fino et al. | 436/537 |
| 4,559,173 | 12/1985 | Flentge | 540/542 |
| 4,593,089 | 6/1986 | Wang et al. | 436/536 |
| 4,952,691 | 8/1990 | Wang et al. | 544/300 |

FOREIGN PATENT DOCUMENTS

| | | |
|---|---|---|
| 56/87559 | 12/1979 | Japan . |
| 57/109724 | 12/1980 | Japan . |

OTHER PUBLICATIONS

A. Sidki et al., Clin. Chem., vol. 30/8, 1348–1352 (1984).
L. Li et al., Epilepsia, vol. 23, 391–398 (1982).
J. Paxton et al., J. Pharmacol. Methods, vol. 3, 289–296 (1980).

Primary Examiner—Mary E. Ceperley

[57] ABSTRACT

An immunoassay method and analytical elements for detecting carbamazepine drugs, for example, in body fluids, is described. The immunoassay method comprises:

(A) contacting a liquid sample, containing carbamazepine, with a labeled carbamazepine analogue in the presence of antibodies for carbamazepine under conditions that promote the formation of carbamazepine/antibody immunocomplexes; and (B) determining the quantity of the drug in the liquid by measuring bound or unbound labeled drug analogue; characterized in that the labeled carbamazepine comprises:

(1) a label, of the type used in immunoassays, having an amine or sulfhydryl group;
(2) a carbamazepine nucleus; and
(3) a linking chain linking the carboxamide group of the carbamazepine nucleus to the label, said linking chain having about 4 to about 40 atoms consisting of:
 (a) alkylene groups; and
 (b) heterocyclic ring groups, each group being joined into the linking group through chemical groups selected from
  (a) esters,
  (b) amides,
  (c) heteroatoms selected from —O—, —S—, and —NR—; wherein each R independently represents hydrogen or $C_1$ to $C_6$ alkyl; and
  (d) carbonyl groups.

The elements of the invention are preferably dry, thin film analytical elements comprising a labeled carbamazepine analogue as described.

13 Claims, No Drawings

IMMUNOASSAYS WITH NOVEL LABELED CARBAMAZEPINE HAPTEN ANALOGUES

RELATED INVENTION

Novel Carbamazepine Hapten Analogues by Ponticello and Saini, filed on even date herewith and Labeled Carbamazepine Hapten Analogues For Competitive Enzyme Immunoassays by Brummond, Saini, and Ponticello, also filed on even date herewith.

1. Field of the Invention

This invention relates to clinical chemistry, particularly immunoassays.

2. Background of the Invention

Immunoassays, which take advantage of natural immunological reactions, have found wide-spread use as analytical techniques in clinical chemistry. Because of the specificity of the reactions, they are particularly advantageous in quantifying biological analytes that are present in very low concentration in biological fluids. Such analytes (called ligands herein) include, for example, antibodies, therapeutic drugs, narcotics, enzymes, hormones, proteins, etc.

In competitive binding immunoassays, a labeled ligand, including immunocompetent derivatives and analogs of the ligand is placed in competition with unlabeled ligand for reaction with a fixed amount of the appropriate binding material (called a receptor herein). Unknown concentrations of the ligand can be determined from the measured signal of either the bound or unbound (i.e. free) labeled ligand. The reaction proceeds as follows:

ligand+labeled ligand+receptor→ ligand-receptor+labeled ligand-receptor.

Conventional labels include radioactive tags, enzymes, chromophores, fluorophores, stable free radicals, and enzyme cofactors, inhibitors and allosteric effectors.

Consistent with the foregoing an immunoassay for ligands such as carbamazepine in serum can be based on competition between (1) an enzyme labeled carbamazepine analogue with (2) the carbamazepine in a patients blood serum for immobilized antibody binding sites.

Specific requirements for the labeled carbamazepine analogue include: 1) at least about 70–90% of the analogue can be bound by excess immobilized carbamazepine antibodies; 2) affinity of the analogue for immobilized antibodies is such that competition of a fixed amount of carbamazepine occurs in a therapeutically relevant concentration range; and 3) stability of the analogue against hydrolysis of its enzyme label under storage conditions. Requirements imposed on the carbamazepine analogue include: 1) accessibility of the derivative to the immobilized antibody following conjugation with the enzyme label; 2) specific recognition of the derivative by the antibody to the carbamazepine; 3) sufficient reactivity of the derivative with the enzyme label, either directly or following activation of the enzyme or derivative, under conditions that do not adversely affect enzyme activity; 4) stability of the label against hydrolysis of the carbamazepine analogue from the enzyme; and 5) fast and complete attachment of the carbamazepine hapten to the enzyme by covalent bonding, without denaturing the enzyme.

STATEMENT OF THE INVENTION

The present invention provides an immunoassay method for carbamazepine comprising:

A. contacting a liquid sample, containing carbamazepine, with a labeled carbamazepine analogue in the presence of antibodies for carbamazepine under conditions that promote the formation of carbamazepine/antibody immunocomplexes; and B. determining the quantity of the drug in the liquid by measuring bound or unbound labeled drug analogue; characterized in that the labeled carbamazepine comprises:
 (1) a label, of the type used in immunoassays, having an amine or sulfhydryl group;
 (2) a carbamazepine nucleus; and
 (3) a linking chain linking the carboxamide group of the carbamazepine nucleus to the label through a carbonyl group, said linking chain having about 4 to about 40 atoms consisting of:
  (a) $C_2$ to $C_6$ alkylene groups; and
  (b) 5 to 7 membered heterocyclic ring groups selected from 1,4-piperazinylene; 2,5-dimethyl-1,4-piperazinylene; 1,3-imidazolidinylene, and 1,3-hexahydrodiazepinylene; each group being joined into the linking group through chemical groups selected from
   (a) esters, including thioesters

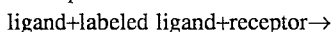

where Z is O or S;
   (b) amides,

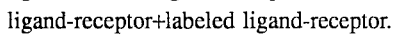

wherein R represents hydrogen or $C_1$ to $C_6$ alkyl
   (c) hetero atoms selected from —O—, —S—, and —NR—; wherein each R independently represents hydrogen or $C_1$ to $C_6$ alkyl; and
   (d) carbonyl.

Useful labeled carbamazepine analogues include those conforming to the structure (I):

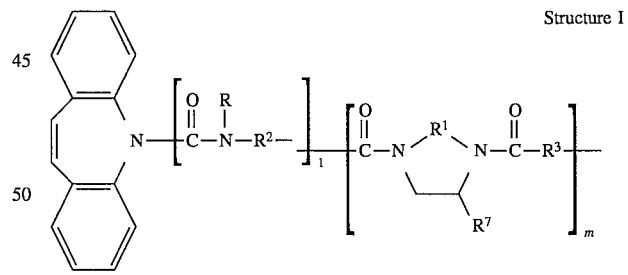

Structure I

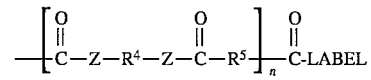

Structure I

R represents hydrogen or lower alkyl of about 1 to 6 carbon atoms $R^1$ is alkylene of 1 to 3 carbon atoms sufficient to form with $R^7$ a heterocylic group selected from 1,4-piperazinylene; 2,5-dimethyl-1,4-piperazinylene; 1,3-imidazolidinylene, and 1,4-hexahydrodiazepinylene;

$R^2$, $R^3$, $R^4$, and $R^5$ each independently represent alkylene groups of about 2 to 10 carbon atoms, or phenylene;

$R^7$ is hydrogen or methyl;

each Z independently represents —O—, —S—, or —NR— wherein R represents hydrogen or lower alkyl of about 1 to 6 carbon atoms:

LABEL is an enzyme l is 0, 1 or 2;

m is 0, 1, or 2;

n is 0, 1, or 2; and (i) the sum of carbon and hetero atoms in the linear chain comprising $R^2$, $R^3$, $R^4$, and $R^5$ the linking atoms which join them (not counting the amide group of the carbamazepine nor the carbonyl joining the label) is about 5 to 40, (ii) provided that the bracketed components of structure I can appear therein in any order, and (iii) only one $R^2$, $R^3$, $R^4$, or $R^5$ group can be phenylene.

The labeled carbamazepine analogues, having short linking chains between the carbamazepine nucleus and labels, such as horseradish peroxidase (HRP) are useful with some immobilized antibodies. Analogues with a longer linking group between the Label and the carbamazepine nucleus were strongly bound by the immobilized antibodies tested. Linking groups having amide bonds instead of ester bonds are resistant to hydrolysis and therefore avoid any problem of separation of the carbamazepine nucleus from the label. The carbamazepine-HRP labels of this invention with extended linkers have the ability to be completely bound (>90%) by all the immobilized antibody types we have prepared. This allows us to pursue a variety of antibodies to develop the carbamazepine enzyme immunoassay.

DETAILS OF THE INVENTION

We have devised a new method for the preparation of labeled carbamazepine analogues used in the immunoassay of this invention. The new method of preparation comprises the steps of:

1) contacting
   (A) a label having an amine or sulfhydryl group thereon, with an excess of a
   (B) carbamazepine analogue comprising:
      (i) an active ester group such as succinimidoxycarbonyl;
      (ii) a carbamazepine nucleus; and
      (iii) a linking chain (i) linking the carboxamide group of the carbamazepine nucleus to the active ester group through a carbonyl group (The linking group is otherwise identical to the linking group defined previously herein); and 2) removing the unused carbamazepine analogue and condensation by-products, preferably by dialysis.

Preferably the step of contacting is carried out by dissolving both the analogue and the label in a water-miscible organic solvent such as N,N-dimethylformamide or dimethyl sulfoxide or a mixture of solvent and water (buffered) before mixing together.

All the labeled carbamazepine analogues prepared by the above method are new chemical compositions of matter and are the subject of U.S. Ser. No. 926,205 filed on even date herewith in the names of Ponticello et al., now U.S. Pat. No. 5,395,933 and is expressly incorporated herein by reference.

The preparation of the intermediate carbamazepine analogues, from which the labeled counterparts are made, are prepared as described in related U.S. Ser. No. 926,203 filed on even date herewith in the name Brummond et al and is expressly incorporated herein by reference. Preparation of such intermediates is presented below.

The following intermediate preparation examples describe the preparation of labeled carbamazepine analogues from the carbamazepine analogues prepared in intermediate examples 1–8, supra.

Preparatory Example 1

N-[2-(3-Succinimidoxycarbonyl-propionyloxy)ethyl]carbamazepine

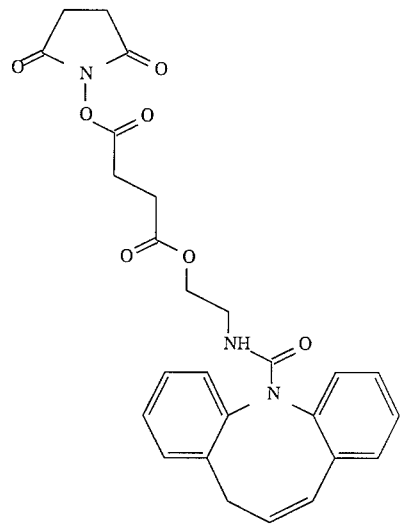

Step 1: Preparation of N-(2-Hydroxyethyl)carbamazepine

A mixture of ethanolamine (6.1 g, 0.1 mole) and 5-chlorocarbonyl-2,2'-iminostilbene (6.5 g, 0,025 mole) in toluene (250 mL) was heated at reflux for 4 hours and then allowed to stand at ambient temperature for 16 hours. To the mixture was added dichloromethane (500 mL), and the solution was washed with 10% hydrochloric acid (2×100 mL), washed with saturated sodium bicarbonate solution (100 mL), washed with saturated sodium chloride solution (100 mL), dried over anhydrous magnesium sulfate, filtered, and the solvent removed on a rotary evaporator.

To the residue was added dichloromethane (45 mL) and ethyl acetate (75 mL), and the mixture was placed in the freezer (−16° C.). The solid was filtered.

Step 2: N-[2-(3-Carboxypropionyloxy)ethyl]carbamazepine

A mixture of N-(2-hydroxyethyl)carbamazepine (5.6 g, 0.02 mole), succinic anhydride (2.2 g, 0.02 mole), and dimethylaminopyridine (2.4 g, 0.02 mole) in chloroform (25 mL) was stirred at ambient temperature for 24 hours. Dichloromethane (400 mL) was added, and the mixture was washed with 10% hydrochloric acid solution (2×100 mL), washed with saturated sodium chloride solution (100 mL), dried over anhydrous magnesium sulfate, filtered, and the solvent removed. To the residue was added ethyl ether (25 mL) and petroleum ether (25 mL). A sample was recrystallized from methanol.

Step 3: N-[2-(3-Succinimidoxycarbonylpropionyloxy)ethyl] carbamazepine

A mixture of N-[2-(3-carboxypropionyloxy)ethyl]carbamazepine (3.8 g, 0.01 mole), N,N'-dicyclohexylcarbodiimide (2.1 g, 0.01 mole), and N-hydroxysuccinimide (1.2 g, 0.01 mole) in chloroform (75 mL) was stirred at room temperature for 20 hours. The mixture was filtered, and the filtrate was concentrated on a rotary evaporator in vacuo to give a white solid. Analytical calculated for $C_{25}H_{23}N_3O_7$: C, 62.89; H, 4.86; N, 8.80. Found C, 60.74: H, 5.12; N, 8.83.

Preparatory Example 2

N-[3-(3-Succinimidoxycarbonylpropionamido)propyl]carbamazepine

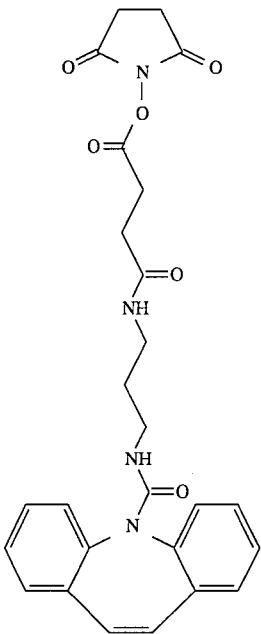

Step 1: N-[3-(Benzyloxycarbonylamino)propyl]carbamazepine

A mixture of N-benzyloxycarbonyl-1,3-propanediamine (8.0 g, 0.04 mole) and triethylamine (5.0 g, 0.05 mole) in chloroform (75 mL) was added dropwise over 15 minutes to 5-chlorocarbonyl-2,2'-iminostilbene (7.6 g, 0.03 mole) in chloroform (200 mL). The mixture was then heated at reflux for 1 hour and at ambient temperature for 16 hours. Dichloromethane (500 mL) was added, and the mixture was washed with 10% hydrochloric acid (2×100 mL), washed with saturated sodium chloride solution (100 mL), dried over anhydrous magnesium sulfate, filtered, and the solvent removed on a rotary evaporator in vacuo. To the residue was added ethyl acetate (50 mL) and the solution placed in the freezer for 2 hours and filtered.

Step 2: N-(3-Aminopropyl)carbamazepine Hydrobromide

N-[3-(Benzyloxycarbonylamino)propyl]carbamazepine (13.2 g, 0.03 mole) and 30–35% hydrogen bromide-acetic acid solution (70 mL) was allowed to stir at room temperature for 1 hour. This mixture was then poured into diethyl ether (3 L), and the solid which forms was triturated with fresh portions of ether (3×1 L). The solid was filtered.

Step 3: N-[3-(3-Carboxypropionamido)propyl]carbamazepine

A mixture of N-(3-aminopropyl)carbamazepine hydrobromide (7.5 g, 0.02 mole), triethylamine (2.0 g, 0.02 mole), and succinic anhydride (2.0 g, 0.02 mole) in chloroform (200 mL) was heated for 30 minutes at 50°–60° C. and allowed to stand at ambient temperature for 20 hours. Dichloromethane (500 mL) was added, and the mixture was washed with 10% hydrochloric acid (2×100 mL) and saturated sodium chloride solution (100 mL), then dried over anhydrous magnesium sulfate, filtered, and the solvent removed on a rotary evaporator in vacuo. To the residue was added dichloromethane (100 mL) and petroleum ether (100 mL), and it was placed in the freezer overnight. The solid was filtered.

Step 4: N-[3-(3-Succinimidoxycarbonylpropionamido)propyl]carbamazepine

A mixture of N-[3-(3-carboxypropionamido)propyl]carbamazepine (3.3 g, 0.01 mole), N,N'-dicyclohexylcarbodiimide (2.0 g, 0.01 mole), and N-hydroxysuccinimide (1.0 g, 0.01 mole) in chloroform (80 mL) was stirred at room temperature for 20 hours. The mixture was filtered and the solvent removed on a rotary evaporator in vacuo to give 4.7 g. The solid was dissolved in dichloromethane (20 mL), filtered and the solvent removed. This procedure was repeated an additional time to give 3.0 g (64% yield). Analytical calculated for $C_{26}H_{26}N_3O_6$: C, 65.54; H, 5.50; N, 8.82. Found: C, 62,38; H, 5.47; N, 11.02.

Preparatory Example 3

N-[3-(4-Succinimidoxycarbonylbutyramido)propyl]carbamazepine

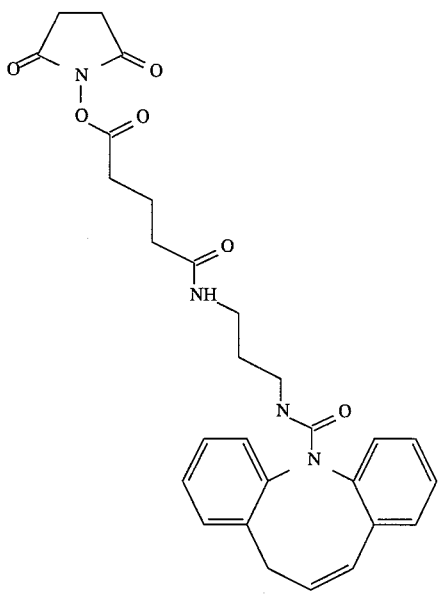

Step 1: N-[3-(4-Carboxybutyramido)propyl]carbamazepine

N-(3-aminopropyl)carbamazepine hydrobromide (4.8 g, 0.0128 mole) was treated with glutaric anhydride (1.5 g, 0.0128 mole), triethylamine (1.4 g, 0.014 mole) by the procedures described in step 3 of Preparatory Example 2.

Step 2: N-[3-(4-Succinimidoxycarbonylbutyramido)propyl]carbamazepine

N-[3-(4-Carboxybutyramido)propyl]carbamazepine was treated with N-hydroxysuccinimide by the procedure described in step 4 of Preparatory Example 2 to give the product. Analytical calculated for $C_{27}H_{28}N_4O_6$: C, 64.28; H, 5.59; N, 11.10. Found: C, 63.84; H, 5.72, N, 10.89.

Preparatory Example 4

N-[6-(4-Succinimidoxycarbonyl-butyramido)hexyl]carbamazepine

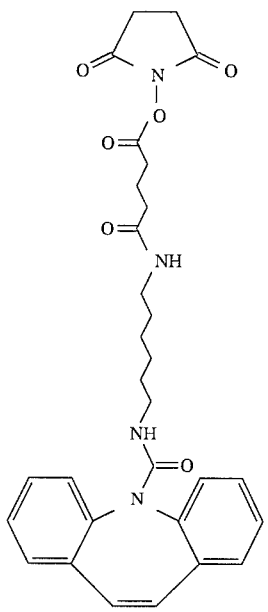

Step 1: N-[6-(Benzyloxycarbonylamino)hexyl]carbamazepine

This material was prepared using the procedure outlined in step 1, Preparatory Example 2, except using N-benzyloxycarbonyl-1,6-hexanediamine in place of the N-benzyloxycarbonyl-1,3-propanediamine, to give 11.0 g (94% yield). Pure material was obtained by crystallization from ethyl acetate/pentane (1:1).

Step 2: N-(6-Aminohexyl)carbamazepine Hydrobromide

This material was prepared using the procedure outlined in Preparatory Example 2, step 2, except substituting N-[6-(benzyloxycarbonylamino)hexyl]carbamazepine for the N-[3-benzyloxycarbonylamino)propyl]carbamazepine, to give 8.5 g (100% yield).

Step 3: N-[6-(4-Carboxybutyramido)hexyl]carbamazepine

This material was prepared using the procedure outlined in step 3, Preparatory Example 2, except substituting N-(6-aminohexyl)carbamazepine hydrobromide and glutaric anhydride, respectively, for the N-(3-aminopropyl)carbamazepine hydrobromide and succinic anhydride. The product was crystallized from dichloromethane/ethyl acetate (1:1).

Step 4: N-[6-(4-Succinimidoxycarbonylbutyramido)hexyl] carbamazepine

This material was prepared using the procedure outlined in Preparatory Example 2, step 4, except substituting N-[6-(4-carboxybutyramido)hexyl]carbamazepine for the N-[3-(3-carboxypropionamido)propyl]carbamazepine. Analytical calculated for $C_{30}H_{34}N_4O_6$: C, 65,92; H, 6.27; N, 10.25. Found: C, 65.20; H, 6.19; N, 10.02.

Preparatory Example 5

5-[4-(4-Succinimidoxycarbonylbutyryl)piperazinocarbonyl]-5H-dibenzo [b,f]azepine

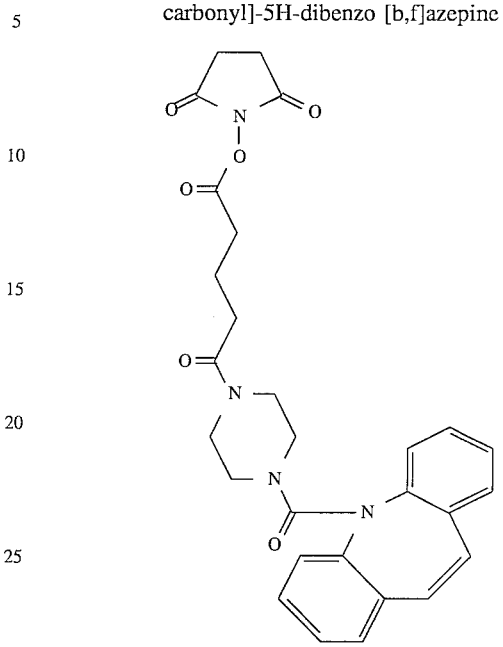

Step 1: 5-[4-(Benzyloxycarbonyl)piperazinocarbonyl]-5H-dibenzo[b,f]azepine

This material was prepared using the procedures outlined in Preparatory Example 2, step 1, except substituting benzyl 1-piperazinecarboxylate in place of the N-benzyloxycarbonyl-1,3-propanediamine.

The compound was dissolved in ethyl ether (10 mL) and petroleum ether was added to the cloud point. The mixture was placed in a freezer, and then filtered to give 9.3 g material.

Step 2A: 5-(Piperazinocarbonyl)-5H-dibenzo[b,f]azepine Hydrobromide
Step 2B: 5-[4-(4-Carboxybutyryl)piperazinocarbonyl]-5H-dibenzo[b,f]azepine These materials were prepared using the procedures outlined in Steps 2 and 3 of Preparatory Example 2, except starting with 5-[4-(benzyloxycarbonyl)piperazinocarbonyl]-5H-dibenzo[b,f]azepine in place of the N-[3-(benzyloxycarbonylamino)propyl]carbamazepine in step 2, and thus the product 5-(Piperazinocarbonyl)-5H-dibenzo-[b,f]azepine Hydrobromide in place of the product of step 2, and glutaric anhydride in place of succinic anhydride in the procedures of step 3. The residue (2 B) was crystallized from ethyl acetate (10 mL) and petroleum ether (2 mL), placed in a freezer, and filtered to give the acid.

Step 3: 5-[4-(3-Carboxypropionyl)piperazinocarbonyl]-5H-dibenzo[b,f]azepine

This material was prepared using the procedures outlined in step 2 B of Preparatory Example 4, except using succinic anhydride in place of glutaric anhydride. A sample recrystallized from dichloromethane/ethyl acetate (1:1) gave pure material.

Step 4: 5-[4-(4-Succinimidoxycarbonylbutyryl)piperazinocarbonyl]-5H-dibenzo[b,f]azepine This material was prepared using the procedure outlined in Preparatory Example 2, step 4, except using 5-[4-(carboxybutyryl)piperazinocarbonyl]5H-dibenzo[b, f]azepine in place of the N-[3-(3-carboxypropionamido)propyl]carbamazepine to give 4.6 g (100% yield). The material (3.0 g) was chromatographed using silica gel. Analytical calculated for $C_{28}H_{28}N_4O_6$: C, 65.09; H, 5.47; N, 10.85. Found: C, 64.87; H, 5.99; N, 10.62.

Preparatory Example 6

5-[4-(3-Succinimidoxycarbonylpropionyl)piperazinocarbonyl]-5H-dibenzo[b, f]azepine

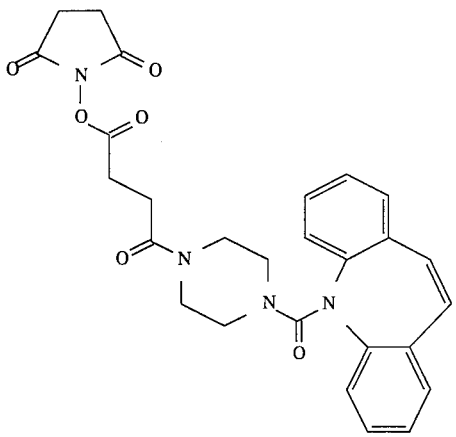

This material was prepared using the procedure outlined in step 4, Preparatory Example 2, except using 5-[4-(3-carboxypropionyl)piperazinocarbonyl]-5H-dibenzo[b,f]azepine in place of the N-[3(3-carboxypropionamido)propyl]carbamazepine. A sample was recrystallized from dichloromethane (35 mL) and ethyl acetate (8 mL) to give material melting at 135°–140° C. Analytical calculated for $C_{27}H_{26}N_4O_6$: C, 64.33; H, 5.22; N, 11.15. Found: C, 62.46; H, 5.29; N, 10.82.

Preparatory Example 7

N-(4-Succinimidoxycarbonylbutyl)carbamazepine

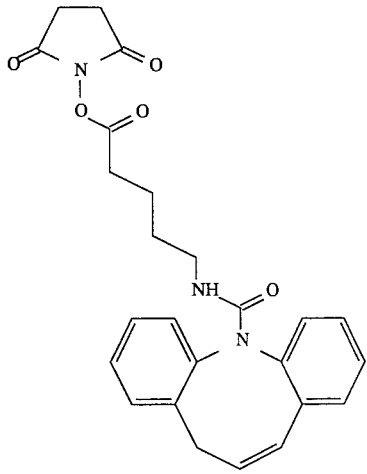

Step 1: N-(4-Methoxycarbonylbutyl)carbamazepine

To a mixture of sodium hydride (6.0 g, 0.2 mole, 80%) and carbamazepine (40.0 g, 0.17 mole) in tetrahydrofuran (400 mL) was added over 30 minutes methyl 5-bromovalerate (39.0 g, 0.19 mole) in tetrahydrofuran (100 mL). The mixture was stirred at ambient temperature for 3 days and then poured into ice containing concentrated hydrochloric acid (100 mL). The aqueous solution was extracted with dichloromethane (3×200 mL), and the combined organic solutions were washed with saturated sodium bicarbonate solution (200 mL), saturated sodium chloride solution (200 mL), then dried over anhydrous magnesium sulfate, filtered, and the solvent removed on a rotary evaporator in vacuo. To the residue was added ethyl ether (100 mL). The mixture was placed in the freezer (–16° C.) and filtered to give a white solid.

Step 2: N-(4-Carboxybutyl)carbamazepine N-(4-Methoxycarbonylbutyl)carbamazepine (6.3 g, 0.18 mole) was dissolved in p-dioxane (120 mL), water (25 mL), and concentrated hydrochloric acid (50 mL). The solution was refluxed for 2 hours and then stirred to ambient temperature. To this mixture was added saturated sodium chloride solution (100 mL) and the mixture extracted with dichloromethane (3×300 mL). The combined organic solutions were washed with saturated sodium chloride solution (100 mL), dried over anhydrous magnesium sulfate, filtered, and the solvent removed. The residue was dissolved in dichloromethane (175 mL) and ethyl acetate (100 mL) was added. The mixture was placed in the freezer (–16° C.) and then filtered.

Step 3: N-(4-Succinimidoxycarbonylbutyl)carbamazepine

This material was prepared using the procedure outlined in Preparatory Example 2, step 4, except using N-(4-carboxybutyl)carbamazepine in place of the N-[3-(3-carboxypropionamido)propyl]carbamazepine. Analytical calculated for $C_{24}H_{23}N_3O_5$: C, 66.50; H, 5.35; N, 9.69. Found: C, 65.82; H, 5.58; N, 9.37.

Preparatory Example 8

N-{4-[4-(3-Succinimidoxycarbonylpropionyl)piperazinocarbonyl]butyl}carbamazepine

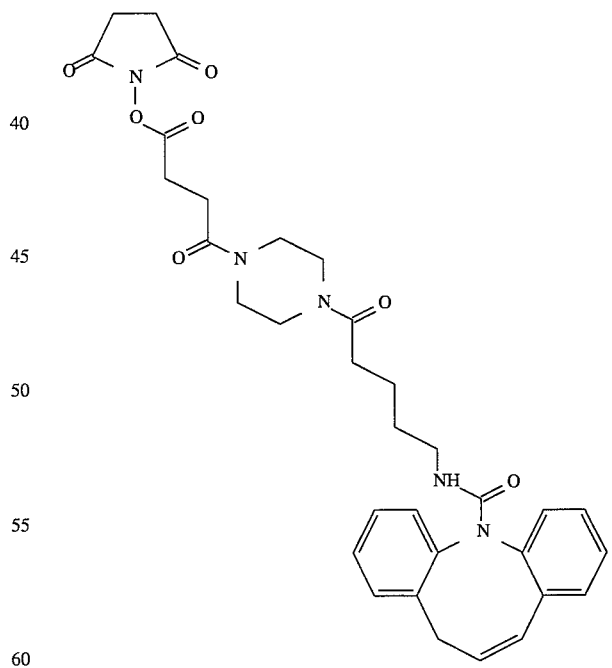

Step 1: N-[4-(4-Benzyloxycarbonylpiperazinocarbonyl)butyl]carbamazepine

A mixture of N-(4-carboxybutyl)carbamazepine (3.4 g, 0.01 mole) and 1,1'-carbonyldiimidazole (2.1 g, 0.0125 mole) in tetrahydrofuran (100 mL) was stirred at ambient temperature for 30 minutes. To this mixture was added at room temperature over 30 minutes benzyl 1-piperazinecarboxylate (2.75 g, 0.0125 mole) in tetrahydrofuran (100 mL). After 20 hours, dichloromethane (300 mL) was added, and the organic solution was washed with 5% hydrochloric acid solution (3×100 mL), washed with saturated sodium carbonate solution (100 mL), washed with saturated sodium chloride solution (100 mL), dried over anhydrous magnesium sulfate, filtered, and the solvent removed on a rotary evaporator in vacuo. The material was used directly in the next step.

Step 2A: N-(4-Piperazinocarbonylbutyl)carbamazepine Hydrobromide

Step 2B: N-{4-[4-(3-Carboxypropionyl)piperazinocarbonyl]butyl}carbamazepine

These materials were prepared using the procedures outlined in steps 2 and 3 of Preparatory Example 2, except starting with N-[4-(4-benzyloxycarbonylpiperazinocarbonyl)butyl]carbamazepine in place of the N-[3-(benzoyloxycarbonylamino)propyl]carbamazepine in step 2A, and then using the product from step 2A of Preparatory Example 8 in place of the product of step 2 of Preparatory Example 2 in step 2B of Preparatory Example 8 to give the acid.

Step 3: N-{4-[4-(3-Succinimidoxycarbonylpropionyl)piperazinocarbonyl]butyl}carbamazepine This material was prepared using the procedure outlined in Preparatory Example 2, step 4, except using N-{4-[4-(3-carboxypropionyl)piperazinocarbonyl]butyl}carbamazepine in place of the N-[3-(3-carboxypropionamido)propyl]carbamazepine. A sample was chromatographed using silica gel to give analytically pure material. Analytical calculated for $C_{32}H_{35}N_5O_7$: C, 63.88; H, 5.86; N, 11.64. Found: C, 63.13; H, 6.02; N, 11.06.

Preparatory Example 9

N-{4-[3-(4-Succinimidoxycarbonylbutyramido)propylaminocarbonyl]butyl}carbamazepine Step 1: N-[4-(3-Benzyloxycarbonylaminopropylaminocarbonyl)butyl]carbamazepine This material was prepared using the procedure outlined in step 1 of Preparatory Example 8, except substituting N-benzyloxycarbonyl-1,3-propanediamine for the benzyl 1-piperazinocarboxylate. The residue was treated with ethyl ether (8 mL), acetone (4 mL), and petroleum ether (3 mL), placed in a freezer (−16° C.), and filtered to give the product.

Step 2A: N-[4-(3-Aminopropylaminocarbonyl)butyl]carbamazepine Hydrobromide

Step 2B: N-{4-(3-(4-Carboxybutyramido)propylaminocarbonyl]butyl}carbamazepine

These materials were prepared using the procedures outlined in steps 2 and 3 of Preparatory Example 2, except substituting N-[4-(3-benzyloxycarbonylaminopropylaminocarbonyl)butyl]carbamazepine in place of the N-[3-(benzyloxycarbonylamino)propyl]carbamazepine in step 2, and N-[4-(3-aminopropylaminocarbonyl)butyl]carbamazepine hydrobromide for the N-(3-aminopropyl)carbamazepine hydrobromide and glutaric anhydride for the succinic anhydride in step 3, to give 2.6 g (44%) yield. The solid was recrystallized from methanol (4 mL) and ethyl acetate (15 mL) to give pure material.

Step 3: N-{4-[3-(4-Succinimidoxycarbonylbutyramido)propylaminocarbonyl]butyl}carbamazepine This material was prepared using the procedures outlined in step 4 of Preparatory Example 2, except substituting N-{4-[3-(4-carboxybutyramido)propylaminocarbonyl]butyl}carbamazepine for the N-[3-(3-carboxypropionamido)propyl]carbamazepine. A sample was chromatographed on silica gel to give a white solid. Analytical calculated for $C_{32}H_{37}N_5O_7$: C, 63.67; H, 6.18; N, 11.60. Found: C, 61.74; H, 6.21; N, 10.77.

Preparatory Example 10

Preparation of N-(4-Succinimidoxycarbonylbutyl)carbamazepine-Amine-Enriched HRP (Horseradish Peroxidase) Conjugate (Label A)

Amine-enriched HRP was prepared as follows. Briefly, dry HRP (horseradish peroxidase) is dissolved in 0.1M MES buffer, pH 5.5, to achieve a final concentration of $2.5 \times 10^{-6}$ mol (100 mg) in 10 mL of buffer (MES=2-(N-morpholino)ethane sulfonic acid). The protein concentration was determined by A403 measurement using the conversion factor A403 1 mg/mL=2.24. The HRP solution was combined with $1.5 \times 10^{-3}$ mol (275 mg) of L-lysine monohydrochloride dissolved in 10 mL of 0.1M MES buffer at pH 5.5. A solution of freshly prepared 1-ethyl-3-(3-dimethylaminopropyl)carbodiimide hydrochloride (EDC, $5 \times 10^{-4}$ mol, 960 mL) in MES buffer was added. The container was capped and mixed overnight at room temperature. The reaction was dialyzed against 0.02M MOPS buffer at pH 7.0 (3 L at 10° C.). The dialysis buffer was changed 3×. MOPS=3-(N-morpholino)propanesulfonic acid.

Prior to reaction, a sample of the amine-enriched HRP was exchanged from MOPS buffer into 0.1M EPPS buffer, pH 8.0, using Centricell Centrifugal Ultrafilter (30,000 nominal molecular weight limit). This sample was then diluted to 5.0 mL to produce a solution with a final concentration of 10.00 mg/mL ($2.5 \times 10^{-4}$M). EPPS is N-(2-hydroxyethyl)piperazine-N,-3-propanesulfonic acid.

One mL of the amine-enriched HRP solution was added to a small vial ($2.5 \times 10^{-4}$M). 500 µL of dimethylformamide, Aldrich 22,705-6, containing 10 mM 4'-hydroxyacetanilide (DMF 4'-HA) was added to the vial, vortexed, and placed in a 42° C. water bath.

Meanwhile, the requiste carbamazepine hapten analogue was dissolved in DMF 4'-HA to yield a 21.54 mg/mL solution ($5.0 \times 10^{-2}$M). 500 µL of this solution was added to the HRP/DMF 4'-HA solution dropwise while vortex mixing. The molar ratio of the carbamazepine/HRP was 100/1.

Incubation was performed at 42° C. for 1 hour with gentle shaking in a water bath. The sample was transferred to Spectrapor #2 dialysis tubing along with an additional 0.5 mL of DMF 4'-HA/0.1M EPPS (1:1) used to rinse the reaction container.

The reaction was dialyzed as follows:
a) 1 L DMF 4'-HA/0.1M EPPS, pH 8.0 (1:1), at 42° C. for 1 hour
b) Dialysis condition a) was repeated 1×
c) 1.5 L 0.1M EPPS, pH 8.0, containing 0.1% bovine serum albumin (BSA) at 5° C., 2 hours
d) 1.5 L 0.1M EPPS, pH 8.0, at 5° C., overnight
e) 2.0 L 40 mM Tris-HCl, 150 mM NaCl, pH 7.5, for at least 8 hours
f) Dialysis condition e) was repeated 1× Tris-HCl is tris(hydroxymethyl)aminomethane hydrochloride. Following dialysis, 0.02% merthiolate was added as a preservative, and the label was stored refrigerated.

Preparatory Example 11

N-[6-(4-Succinimidoxycarbonylbutyramido)hexyl]carbamazepine Amine-Enriched HRP (Label B)

Amine-enriched HRP was prepared as described in Preparatory Example 10. Prior to reaction, a sample of the amine-enriched HRP was exchanged from MOPS buffer into 0.1M EPPS buffer, pH 8.0, using Centricell Centrifugal Ultrafilter (30,000 nominal molecular weight limit). This sample was then diluted to 3.0 mL to produce a solution with a final concentration of 8.36 mg/mL ($2.08\times10^{-4}$M). EPPS is N-(2-hydroxyethyl)piperazine-N'-3-propanesulfonic acid.

To prepare Label B, one mL of amine-enriched HRP was added to a small vial ($1.85\times10^{-5}$M). 500 μL of dimethylformamide, Aldrich 22,705-6, containing 10 mM 4'-hydroxyacetanilide (DMF 4'-HA) was added to the vial, vortexed, and placed in a 42° C. water bath.

Meanwhile, the requiste carbamazepine drug hapten analogue was dissolved in DMF 4'-HA to yield a 22.72 mg/mL solution ($4.16\times10^{-2}$M). 500 μL of this solution was added to the HRP/DMF 4'-HA solution dropwise while vortex mixing. The molar ratio of the carbamazepine/HRP was 100/1.

Incubation was performed at 42° C. for 1 hour with gentle shaking in a water bath. The sample was transferred to Spectrapor #2 dialysis tubing along with an additional 1 mL of DMF 4'-HA/0.1M EPPS (1:1) used to rinse the reaction container.

The reaction was dialyzed and stored as described in Preparatory Example 10.

Preparatory Example 12

N-{4-[4-(3-Succinimidoxycarbonylpropionyl)piperazinocarbonyl]butyl}carbamazepine-Amine-Enriched HRP (Label C); and
N-{4-[3-(4-Succinimidoxycarbonylbutyramido)propylaminocarbonyl]butyl}carbamazepine-Amine-Enriched HRP (Label D)

Amine-enriched HRP was prepared as described in Preparatory Example 10 and exchanged into 0.1M EPPS buffer, pH 8.0, using Diaflo Ultrafilters YM30 filters (30,000 molecular weight cutoff) in Amicon Stirred Ultrafiltration Cells. This sample was then diluted to 3.18 mL to produce a solution with a final concentration of 10.00 mg/mL ($2.5\times10^{-4}$M).

One mL of amine-enriched HRP was added to each of two small vials. 500 μL of dimethylformamide, Aldrich 22,705-6, was added to each vial, vortexed, and placed in a 42° C. water bath for at least 15 minutes.

Meanwhile, Succinimidoxycarbonylpropionyl)piperazinocarbonyl]butyl}carbamazepine was dissolved in DMF to yield a 30.05 mg/mL solution ($2.5\times10^{-2}$M). To prepare Label C, 500 μL of this solution was added to the HRP/DMF solution dropwise while vortex mixing. Label D was prepared in the same manner, however, the hapten drug analogue N-{4-[3-(3-Succinimidoxycarbonylbutyramido)propylaminocarbonyl]butyl}carbamazepine was dissolved in DMF to 30.15 mg/mL ($2.5\times10^{-2}$M). The carbamazepine/HRP ratio for both labels is 100/1.

Incubation was performed at 42° C. for 1 hour with gentle shaking in a water bath. The samples were transferred to Spectrapor #2 dialysis tubing along with an additional 1 mL of DMF/0.1M EPPS (1:1) used to rinse the reaction container.

Each reaction mixture was dialyzed as follows:

a) 1 L DMF/0.1M EPPS, pH 8.0 (1:1), at 42° C. for 1 hour
b) Dialysis condition a) was repeated 1×
c) 2.0 L 0.1M EPPS, pH 8.0, containing 0.1% bovine serum albumin (BSA) at 8° C., overnight
d) 2.0 L 0.02M MOPS, pH 7.0, at 8° C., 8 hours
e) Dialysis condition d) was repeated 2×, overnight and 8 hours Following dialysis, 0.02% merthiolate was added as a preservative, and the label was stored refrigerated.

Preparatory Example 13

Preparation of Carbamazepine-Amine-Enriched HRP Labels E, F, and G

N-[6-(4-Succinimidoxycarbonylbutyramido)hexyl]carbamazepine-amine enriched HRP (Label E);
N-{4-[4-(3-Succinimidoxycarbonylpropionyl)piperazinocarbonyl]butyl}carbamazepine-amine enriched HRP (F); and
N-{4-[3-(4-Succinimidoxycarbonylbutyramido)propylaminocarbonyl]butyl)carbamazepine-amine-enriched HRP (Label G)

Amine-enriched HRP was prepared as described in Preparatory Example 10 and exchanged into 0.1M EPPS buffer, pH 8.0, to yield several mL of a 10.00 mg/mL solution ($2.48\times10^{4}$M). Three labels were prepared with 1 mL of amine-enriched HRP each. 500 μL DMSO, was added dropwise with vortex mixing to each sample. The samples were preincubated at room temperature for at least 20 minutes with shaking at 2400 rpm.

Meanwhile, N-[6-(4-Succinimidoxycarbonylbutyramido)hexyl]carbamazepine was dissolved in DMSO to yield a 27.08 mg/mL solution ($2.48\times10^{2}$M). Label E was made by adding 500 μL of this solution to one of the HRP/DMSO solutions prepared above. The hapten was added dropwise while vortex mixing. The Labels F and G were prepared as described above, but the hapten solutions were made as follows:

N-(4-[4-(3-Succinimidoxycarbonylpropionyl)piperazinocarbonyl]butyl}carbamazepine was dissolved to 29.81 mg/mL ($2.48\times10^{2}$M) and used to make Label F; N-{4-[3-(4-Succinimidoxycarbonylbutyramido)propylaminocarbonyl]butyl}carbamazepine was dissolved to 29.81 mg/mL ($2.48\times10^{2}$M) and used to make Label G. The molar ratio of all three labels was 100/1 carbamazepine to HRP.

Incubation was performed at room temperature for 4 hours with shaking at 2400 rpm. The samples were each transferred to Spectrapor #2 dialysis tubing along with an additional 1 mL of dialysate to rinse the reaction containers. The labels were dialyzed into 0.02M MOPS buffer, pH 7.0, at 5°–10° C. This dialysis condition was repeated 3× with 2 to 3 L of buffer each time. Following dialysis, 0.02% merthiolate was added as a preservative, and the labels were stored refrigerated.

The immunoassay of this invention can be carried out in solution or on dry analytical elements.

The dry elements are generally considered to be more convenient. They can be single or multilayer or a combination of layers having zones within such layers. In general the elements can comprise a radiation transmissive support, one or more reagent layers, a particulate spreading layer preferably comprising beads upon which antibodies to the particular carbamazepine analyte are immobilized.

The layers can be coated using well known coating techniques in this art. For example, slide-extrusion hoppers of the type described in U.S. Pat. No. 2,761,417 are often advantageous for simultaneous coating of a plurality of layers at least one of which is comprised of polymeric particles bearing immobilized antibody beads. More particularly, a multilayer element can be coated by directing a coating composition containing the beads through an extrusion slot of a slide extrusion hopper and simultaneously flowing a layer of a second coating composition, which, if desired, may also contain beads down a slide surface of the slide-extrusion hopper.

The particulate layer in which the antibodies are immobilized is porous. Materials for use in such layers are well known in the art of making dry analytical elements. A preferred particulate layer is a bead spreading layer (BSL). This layer can be easily constructed to have suitable porosity for use in the elements of the present invention to accommodate a test sample (e.g. 1 to 100 µL), diluted or undiluted. Preferably, the spreading layer is isotropically porous, which property is created by interconnected spaces between the particles comprising the zone. By isotropically porous is meant that the spreading layer uniformly spreads the applied fluid radially throughout the layer.

Useful particulate spreading layers, including bead spreading layers are disclosed in U.S. Pat. Nos. 4,670,381; 4,258,001 and 4,430,436.

The particulate layer of the element is carried on a suitable support. Such a support can be any suitable dimensionally stable, and preferably, nonporous and transparent (i.e. radiation transmissive) material which transmits electromagnetic radiation of a wavelength between about 200 and about 900 nm. A support of choice for a particular element should be compatible with the intended mode of detection (reflection, transmission or fluorescence spectroscopy). Useful support materials include polystyrene, polyesters [e.g. poly(ethylene terephthalate)], polycarbonates, cellulose esters (e.g. cellulose acetate), etc.

The element can comprise one or more additional layers, e.g. separate or combined reagent/spreading layer and a gelatin/buffer layer containing other necessary additives, coupling enzymes, etc.

The gelatin/buffer layer or the reagent layer or the spreading layer of the element can contain the indicator composition comprising one or more reagents dispersed in one or more synthetic or natural binder materials, such as gelatin, or other naturally-occurring colloids, homopolymers and copolymers, such as poly(acrylamide), poly(vinyl pyrrolidone), poly(N-isopropylacrylamide), poly(acrylamide-co-N-vinyl-2-pyrrolidone) and similar copolymers.

Other optional layers, e.g. subbing layers, radiation-blocking layers, etc. can be included if desired. All layers of the element are in fluid contact with each other, meaning that fluids and reagents and uncomplexed reaction products in the fluids can pass between superposed regions of adjacent layers.

The layers of the element can contain a variety of other desirable but optional components, including surfactants, thickeners, buffers, hardeners, antioxidants, coupler solvents, and other materials known in the art. The amounts of these components are also within the skill of a worker in the art.

The elements can be used to determine low concentrations of carbamazepine in a liquid, such as a biological fluid (e.g., whole blood, serum, plasma, urine, spinal fluid, suspensions of human or animal tissue, feces, saliva, lymphatic fluid and the like). The carbamazepine can be determined at concentrations as low as about $10^{15}$ molar, and most generally at a concentration of from about $5.0\times10^{-6}$ to about $10^{-4}$ molar.

The assay can be carried out using any suitable label which can be attached to the defined carbamazepine analogues. Useful labels include radioactive tags, dyes, fluorescers, enzymes, enzyme substrates, enzyme inhibitors, allosteric effectors, cofactors, coenzymes and other known enzyme modulators. Enzymes, such as glucose oxidase, peroxidases such as horseradish peroxidase and amine-enriched horseradish peroxidase, alkaline phosphatase and galactosidase are preferred labels.

When an enzyme label is used, the substrate for the enzyme is present in the element or added thereto in the developing liquid. The substrate can be added to the element prior to or simultaneously with the liquid sample, or after completion of the binding reaction. It is within the skill of the ordinary worker in clinical chemistry to determine a suitable substrate for a given label. The substrate can be a material which is directly acted upon by the enzyme label, or a material that is involved in a series of reactions which involve enzymatic reaction of the label. For example, if the enzyme label is a peroxidase, the substrate is hydrogen peroxide. Using glucose oxidase as an example, the substrate glucose is generally present in the reagent layer or is added in the developing liquid to yield about 0.01 moles/m$^2$, and preferably from about 0,001 to about 0.1 mole/m$^2$. A worker skilled in the art would know how to adjust the amount of a particular substrate for the amount of enzyme label used in the assay.

When certain labels are used, e.g. enzymes, cofactors, enzyme substrates or enzyme modulators, the reagent layer contains an indicator composition comprising one or more reagents which provide a detectable species as a result of reaction of the label. Preferably, the indicator composition is a colorimetric indicator composition which provides a colorimetrically detectable species as a result of enzymatic reaction of an enzyme-labeled ligand analog with a substrate.

The indicator composition can be a single compound which produces a detectable dye upon enzymatic reaction, or a combination of reagents which produce the dye. For example, when glucose is used as the substrate and glucose oxidase as the enzyme label, the colorimetric indicator composition can include a coupler and oxidizable compound which react to provide a dye. Alternatively, the composition can include a leuco dye and peroxidase or another suitable peroxidative compound which generates a detectable dye as a result of the formation of hydrogen peroxide produced when glucose oxidase converts glucose to gluconic acid. Useful leuco dyes are known in the art and include those, for example, described in U.S. Pat. No. 4,089,747 (issued May 16, 1978 to Bruschi) and U.S. Ser. No. 612,509, filed May 21, 1984 by Babb et al. The particular amounts of the colorimetric indicator composition and its various components are within the skill of a worker in the art.

The immunoassay can be manual or automated. In general, the amount of a ligand in a liquid is determined by taking the element from a supply roll, chip packet or other source and physically contacting a finite area of the spreading layer with a sample of the liquid, e.g. 1 to 100 µl. The finite area which is contacted is generally no more than about 100 mm$^2$.

The amount of ligand is determined by passing the element through a suitable apparatus for detecting the complexed ligand analog directly or the detectable species formed as a result of enzymatic reaction of an enzyme label and a substrate. For example, the species can be detected with suitable radiometric, fluorometric or spectrophotometric apparatus using generally known procedures. In an enzymatic reaction, the resulting product is determined by measuring, for example, the reflection or transmission density or fluorescence in the center of the finite area which was contacted with the test sample. The area which is measured is generally from about 3 to about 5 mm in diameter for competing assays. The amount of ligand in the liquid sample is inversely proportional to the amount of label measured in the center of the finite area. In a preferred embodiment a separate developer step is required in order to maximize separation of complexed ligand from uncomplexed ligand. Generally, label measurement is carried out after from about 5 to about 180 seconds after sample contact and spreading or application of the developing liquid.

The following examples demonstrate the utility of the immunoassay of the present invention using the novel labeled carbamazepine analogues.

The following utility examples demonstrate the utility of the immunoassay of the invention conveniently on dry immunoassay elements.

Example 1

Performance of Carbamazepine-Amine-Enriched HRP Conjugates from Preparative Examples 10 to 13, Labels A to G Immobilized antibody beads were prepared by covalently attaching a carbamazepine monoclonal antibody (Kallestad prod. no. 330509) to poly[styrene-co-4-(2-chloroethylsulfonylmethyl)styrene](weight ratio 90/10) polymer beads of 0.47 μm average diameter.

The ability of immobilized carbamazepine antibody to bind carbamazepine-HRP labels was determined as indicated below:

The antibody beads were serially diluted with PBS containing 0.1% bovine serum albumin (BSA) to give antibody concentrations between 242 and 0.242 nM antibody binding sites. The bead dilutions were mixed with equal volumes of carbamazepine-HRP labels at $10 \times 10^{-11}$M. Following a 1 hour incubation, the beads were pelleted by centrifugation. A sample (100 μL) of the supernatant was mixed with 100 μL of substrate (o-phenylenediamine/$H_2O_2$). The rates of color development at 450 nm were compared with those of standards to calculate the amount of carbamazepine-HRP label remaining in solution. The amount of label bound to immobilized antibody at the highest antibody concentration of 121 nM binding sites is reported. The concentration of antibody binding sites where 50% of the label is bound is also reported.

| | Preparative Example No. | | | | |
|---|---|---|---|---|---|
| Hapten Analog | Label | Preparation Label | tion Solvent | % Label Bound at 121 nM Binding Sites | Ab Binding Sites at 50% Label |
| 7 | 10 | A | DMF | 18 | NA |
| 4 | 11 | B | DMF | 75 | 10.06 nM |
| 8 | 12 | C | DMF | 95 | 2.38 nM |
| 9 | 12 | D | DMF | 94 | 3.23 nM |
| 4 | 13 | E | DMSO | 85 | 5.55 nM |
| 8 | 13 | F | DMSO | 96 | 2.55 nM |
| 9 | 13 | G | DMSO | 97 | 2.47 nM |

Labels having haptens with longer linkers and which contain piperazine are recognized better by the antibody. The percent label bound increases as linker length increases. Label E, made using DMSO, performed better than Label B. Preparations made using DMSO perform better than those made in DMF. DMSO allows for a more simple dialysis purification and results in improved or comparable performance.

Example 2

Use of a Carbamazepine-HRP Label Prepared with an Extended Linker in an Enzyme Immunoassay for Carbamazepine (CBZ)

This example demonstrates the preparation of an analytical element of this invention and its use in a competitive binding assay to detect the drug carbamazepine.

The immunoassay element was prepared to have the following structure using known technology described in the U.S. Pat. Nos. 4,670,381; 4,258,001 and 4,430,436.

| | | Coverage (g/m²) |
|---|---|---|
| Spreading Layer | Immobilized Kallestad 330509 Antibody* | 0.2 |
| | Particles of poly[m- & p-vinyl toluene (64:36)-co-methacrylic acid] (98:2 weight ratio)(30 μm) | 130 |
| | 4,5-bis(4-dimethylaminophenyl)-2-(4-hydroxy-3,5-dimethoxyphenyl)imidazole leuco dye | 0.2 |
| | poly(methyl acrylate-co-sodium 2-acrylamido-2-methylpropane-sulfonate-co-2-acetoacetoxyethyl methacrylate) (90:4:6 weight ratio) | 2.58 |
| | N-[tris(hydroxymethyl)methyl]-2-aminoethanesulfonic acid; (pH 7.0) | 0.219 |
| | dimethyl sulfoxide | 1.8 |
| | 5,5-dimethyl-1,3-cyclohexane dione | 0.50 |
| | Zonyl ™ FSN nonionic surfactant (DuPont) | 0.054 |
| Gelatin Layer | hardened gelatin | 10 |
| | 4'-hydroxyacetanilide | 0.15 |
| | N-[tris(hydroxymethyl)methyl]-2-aminoethanesulfonic acid (pH 7.0) | 4.58 |
| | Triton ™ X-100 nonionic surfactant (Rohm & Haas) | 0.02 |
| | Poly(ethylene terephthalate) Support | |

*The antibody was immobilized on poly[styrene-co-4-(2-chloroethylsulfonylmethyl)styrene] (weight ratio 90/10) polymer beads of about 0.47 μm average diameter by procedures as described by USSN 081,206 filed August 3, 1987 (published EPA 88 307172.2).

A series of human serum based calibrators containing CBZ and a CBZ-HRP label (label C from Preparative Example 12) was prepared. The concentration of CBZ varied from 0.0 to 18.7 μg/mL. The CBZ-HRP label was added to give a final concentration of 2 nM.

The series of CBZ standards (10 mL aliquots) was spotted onto the spreading layers of a series of analytical elements. After 5 minutes incubation at 37° C., a wash solution (10 μL) comprising hydrogen peroxide (0.03%), sodium phosphate buffer (0.01M, pH 6.8), 4'-hydroxyacetanilide (5 mM), diethylenetriaminepentaacetic acid (10 μM) and 0.1% 1-hexadecylpyridinium chloride was added to initiate dye formation. After about 1 minute, the reflection density ($D_r$) was measured at the center of the area at 680 nm at 37° C. The $D_r$ values were converted to $D_t$ by the Clapper-Williams transform. The change in $D_t$ over 60 seconds was calculated. The results are shown below:

| CBZ, μg/mL | Rate ($D_t$/min) |
|---|---|
| 0.0 | 0.1058 |
| 1.8 | 0.0466 |
| 5.0 | 0.0194 |
| 11.6 | 0.0086 |
| 18.7 | 0.0061 |

The results show that there is significant change in rates over the desired dynamic range. The therapeutic range is 8–12 μg/mL.

Example 3

Use of a Carbamazepine-HRP Label Prepared with an Extended Linker in an Enzyme Immunoassay for Carbamazepine (CBZ)

This example demonstrates the preparation of an analytical element of this invention and its use in a competitive binding assay to detect the drug carbamazepine.

The element was prepared using known technology to have the following structure:

| | | Coverage (g/m²) |
|---|---|---|
| Spreading Layer | Immobilized 16.7.1 Antibody* | 0.2 |
| | Particles of poly[m- & p-vinyltoluene (64:36)-co-methacrylic acid] (98:2 weight ratio)(30 μm) | 130 |
| | 4,5-bis(4-dimethylaminophenyl)-2-(4-hydroxy-3,5-dimethoxyphenyl)-imidazole leuco dye | 0.2 |
| | poly(methyl acrylate-co-sodium 2-acrylamido-2-methyl-propane-sulfonate-co-2-acetoacetoxyethyl methacrylate) (90:4:6 weight ratio) | 2.58 |
| | N-[tris(hydroxymethyl)methyl]-2-aminoethanesulfonic acid; (pH 7.0) | 0.219 |
| | dimethyl sulfoxide | 1.8 |
| | 5,5-dimethyl-1,3-cyclohexanedione | 0.50 |
| | Zonyl ™ FSN nonionic surfactant (DuPont) | 0.054 |
| Gelatin Layer | hardened gelatin | 10 |
| | 4'-hydroxyacetanilide | 0.15 |
| | N-[tris(hydroxymethyl)methyl]-2-aminoethanesulfonic acid (pH 7.0) | 4.58 |
| | Triton ™ X-100 nonionic surfactant (Rohm & Haas) | 0.02 |
| | Poly(ethylene terephthalate) Support | |

*The antibody 16.7.1 was prepared and immobilized as described by USSN 539,774 and 654,112 on poly(styrene-co-3-(p-vinylbenzylthio)propionic acid) (molar ratio 97.6/2.4; weight ratio 95/5) beads.

A series of human serum based calibrators containing CBZ and a CBZ-HRP label (label D from Preparative Example 12) was prepared. The concentration of CBZ varied from 0.0 to 18.7 μg/mL. The CBZ-HRP label was added to give a final concentration of 2 nM.

The series of CBZ standards (10 μL aliquots) was spotted onto the spreading layers of a series of analytical elements. After 5 minutes incubation at 37° C., a wash solution (10 μL) comprising hydrogen peroxide (0.03%), sodium phosphate buffer (0.01M, pH 6.8), 4'-hydroxyacetanilide (5 mM), diethylenetriaminepentaacetic acid (10 μM) and 0.1% 1-hexadecylpyridinium chloride was added to initiate dye formation. After about 1 minute, the reflection density ($D_r$) was measured at the center of the area at 680 nm at 37° C. The $D_r$ values were converted to $D_t$ by the Clapper-Williams transform. The change in $D_t$ over 60 seconds was calculated. The results are shown below:

| CBZ, μg/mL | Rate ($D_t$/min) |
|---|---|
| 0.0 | 0.0896 |
| 1.8 | 0.0861 |
| 5.0 | 0.0515 |
| 11.6 | 0.0265 |
| 18.7 | 0.0129 |

The results show that there is significant change in rates over the desired dynamic range. The therapeutic range is 8–12 μg/mL.

The invention has been described in detail with particular reference to preferred embodiments thereof, but it will be understood that variations and modifications can be effected within the spirit and scope of the invention.

What is claimed is:

1. An immunoassay method for carbamazepine comprising:

A. contacting a liquid sample, containing carbamazepine, with a labeled carbamazepine analogue in the presence of antibodies for carbamazepine under conditions that promote the formation of carbamazepine/antibody immunocomplexes; and B. determining the quantity of the drug in the liquid by measuring bound or unbound labeled drug analogue; wherein the labeled carbamazepine analogue 1 has the structure (I):

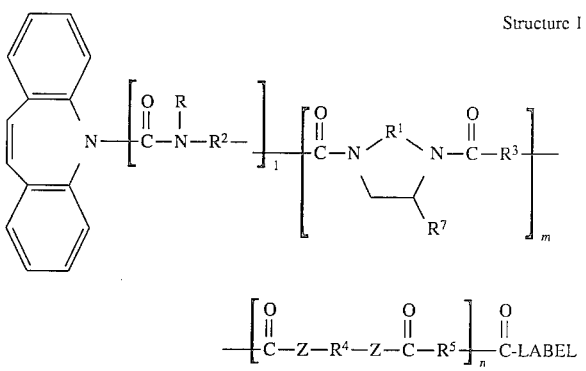

Structure I

R represents hydrogen or lower alkyl of 1 to 6 carbon atoms $R^1$ is alkylene of 1 to 3 carbon atoms sufficient to form a heterocyclic group selected from 1,4-piperazinylene; 2,5-dimethyl-1,4-piperazinylene; 1,3-imidazolidinylene, and 1,4-hexahydrodiazepinylene;

$R^2$, $R^3$, $R^4$, and $R^5$ each independently represent alkylene groups of 2 to 10 carbon atoms, or phenylene;

$R^7$ is hydrogen or methyl;

each Z independently represents —O—, —S—, or —NR— wherein R represents hydrogen or lower alkyl of 1 to 6 carbon atoms:

LABEL is an enzyme;

1 is 0, 1 or 2;

m is 1 or 2;

n is 0, 1, or 2; and (i) the sum of carbon and hetero atoms in the linking chain, comprising the atoms included in $R^2$, $R^3$, $R^4$, and $R^5$, excluding the amide group of carbamazepine and the carbonyl group joining the label to the linking chain, is 5 to 40, (ii) provided that the bracketed components 1, m and n of structure I can appear therein in any order, and (iii) only one $R^2$, $R^3$, $R^4$, or $R^5$ group can be phenylene.

2. The immunoassay method of claim 1 wherein:

$R^1$ represents ethylene thereby forming, with the atoms to which it is bonded, a 1,4-piperazinylene ring group;

$R^2$, $R^3$, $R^4$, and $R^5$ each independently, represent methylene, ethylene, trimethylene, tetramethylene, pentylene, or hexylene; and each Z independently represents —O—, or —NH—.

3. The immunoassay method of claim 2 wherein $R^1$ is ethylene, $R^2$ is tetramethylene, $R^3$ is ethylene, propylene, or hexylene, $R^4$ and $R^5$ are independently ethylene, trimethylene or hexylene, $R^7$ is hydrogen, Z is —O— or —NH—.

4. The immunoassay of claim 3 wherein the label is selected from horseradish peroxidase (HRP) or amine enriched horseradish peroxidase (AHRP).

5. The method of any one of the preceding claims carried out on an immunoassay element.

6. The method of any one of claims 2–4 and 1 carried out on an immunoassay element containing the antibodies in one layer or zone and a separate layer or zone containing the labeled carbamazepine analogue.

7. The method of any one of claims 2–4 and 1 wherein the method is carried out on an immunoassay element in which the antibodies are immobilized on beads in a particulate layer and the labeled analogue is in a coating directly above the layer containing the antibodies.

8. An immunoassay element having a layer, zone or coating of a labeled carbamazepine described in any one of claims 2–4 and 1.

9. The immunoassay of any one of claims 2 to 4 wherein the labeled carbamazepine analogue is a conjugate of amine enriched horseradish peroxidase and the carbamazepine analogue N-{4-[4-(3-Succinimidoxycarbonylpropionyl)piperazinocarbonyl]butyl}carbamazepine.

10. An immunoassay method for carbamazepine, comprising the steps:
   A. contacting a liquid sample, containing carbamazepine, with a labeled carbamazepine analogue in the presence of antibodies for carbamazepine under conditions that promote the formation of carbamazepine antibody immuno complexes;
   B. applying a developing liquid to separate complexed labeled carbamazepine from uncomplexed labeled carbamazepine; and
   C. determining the quantity of the drug in the liquid by measuring bound or unbound labeled drug analogue; wherein the labeled carbamazepine analogue labeled carbamazepine analogue is a conjugate of amine enriched horseradish peroxidase and a member selected from the group consisting of N-[6-(4Succinimidoxycarbonylbutyramido)hexyl]-carbamazepine; and N-{4-[3-(4-Succinimidoxycarbonylbutyramido)propylaminocarbonyl]butyl}carbamazepine.

11. The immunoassay of claim 5 wherein the labeled carbamazepine analogue is a conjugate of amine enriched horseradish peroxidase and the carbamazepine analogue N-{4-[4-(3-Succinimidoxycarbonylpropionyl)piperazinocarbonyl]butyl}carbamazepine.

12. The immunoassay of claim 6 wherein the labeled carbamazepine analogue is a conjugate of amine enriched horseradish peroxidase and the carbamazepine analogue N-{4-[4-(3-Succinimidoxycarbonylpropionyl)piperazinocarbonyl]butyl}carbamazepine.

13. The immunoassay of claim 7 wherein the labeled carbamazepine analogue is a conjugate of amine enriched horseradish peroxidase and the carbamazepine analogue N-{4-[4-(3-Succinimidoxycarbonylpropionyl)piperazinocarbonyl]butyl}carbamazepine.

* * * * *